(12) United States Patent
Schraven

(10) Patent No.: US 10,993,685 B2
(45) Date of Patent: May 4, 2021

(54) DEVICE FOR REMOTE FLUOROSCOPY, NEARBY FLUOROSCOPY AND RADIOLOGY

(71) Applicant: KONINKLIJKE PHILIPS N.V., Eindhoven (NL)

(72) Inventor: Eckhardt Henricus Matheus Schraven, Boxtel (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 187 days.

(21) Appl. No.: 15/744,556

(22) PCT Filed: Jul. 13, 2016

(86) PCT No.: PCT/EP2016/066701
§ 371 (c)(1),
(2) Date: Jan. 12, 2018

(87) PCT Pub. No.: WO2017/009398
PCT Pub. Date: Jan. 19, 2017

(65) Prior Publication Data
US 2018/0199901 A1    Jul. 19, 2018

(30) Foreign Application Priority Data
Jul. 16, 2015  (EP) .................................... 15177096

(51) Int. Cl.
*A61B 6/00*     (2006.01)
*A61B 6/04*     (2006.01)

(52) U.S. Cl.
CPC .......... *A61B 6/4441* (2013.01); *A61B 6/0487* (2020.08); *A61B 6/4405* (2013.01); *A61B 6/4452* (2013.01); *A61B 6/4464* (2013.01)

(58) Field of Classification Search
None
See application file for complete search history.

(56) References Cited

U.S. PATENT DOCUMENTS 3,281,598 A    10/1966  Hollstein
4,412,346 A    10/1983  Takenouti
(Continued)

FOREIGN PATENT DOCUMENTS

JP    2005237678 A    9/2005
JP    2014171537 A    9/2014

*Primary Examiner* — David P Porta
*Assistant Examiner* — Djura Malevic
(74) *Attorney, Agent, or Firm* — Larry Liberchuk

(57) ABSTRACT

The invention concerns a device (102) for X-ray imaging, comprising a device mount (104) and an arm (106) movably connected to said device mount for rotation, relative to said device mount, around a device axis of rotation (108). The device (102) furthermore comprises an X-ray source (110) for emitting an X-ray beam (111) and an X-ray detector (112). In addition the system (102) comprises a carrier (114) having a U-arm geometry, wherein said U-arm geometry is provided with mutually facing portions (116, 118) and an intermediate portion (120) connecting said mutually facing portions (116, 118); wherein said mutually facing portions (116, 118) are configured for carrying said X-ray source (110) and said X-ray detector (112), respectively; and wherein said intermediate portion is movably connected to the arm (106) for rotation, relative to said arm (106), around a carrier axis of rotation (122) substantially perpendicular to the device axis of rotation (108).

12 Claims, 5 Drawing Sheets

(56) References Cited

U.S. PATENT DOCUMENTS

| | | | |
|---|---|---|---|
| 4,481,657 A | 11/1984 | Larsson | |
| 4,501,011 A | 2/1985 | Hauck | |
| 4,894,855 A | 1/1990 | Kresse | |
| 5,155,757 A * | 10/1992 | Sakaniwa | A61B 6/4464 378/196 |
| 5,230,112 A | 7/1993 | Harrawood | |
| 5,386,453 A * | 1/1995 | Harrawood | A61B 6/0442 378/193 |
| 6,644,852 B2 | 11/2003 | Crain | |
| 7,016,457 B1 * | 3/2006 | Senzig | A61B 6/032 378/116 |
| 7,338,207 B2 * | 3/2008 | Gregerson | A61B 6/032 378/17 |
| 7,354,196 B2 * | 4/2008 | Boese | A61B 6/032 378/189 |
| 7,500,783 B2 * | 3/2009 | Kalender | A61B 6/032 378/197 |
| 7,641,391 B2 * | 1/2010 | Schwieker | A61B 6/4464 378/197 |
| 7,837,385 B2 * | 11/2010 | Klingenbeck-Regn | A61B 6/102 378/197 |
| 7,857,512 B2 | 12/2010 | Camus | |
| 8,848,874 B2 * | 9/2014 | Kargar | A61B 6/102 378/117 |
| 9,298,194 B2 * | 3/2016 | Lee | A61B 6/4441 |
| 9,737,275 B2 | 8/2017 | Noda | |
| 9,808,211 B2 * | 11/2017 | Yorkston | A61B 6/032 |
| 9,833,215 B2 * | 12/2017 | Stopp | A61B 6/4452 |
| 2001/0022834 A1 * | 9/2001 | Graumann | A61B 6/4405 378/198 |
| 2001/0027263 A1 * | 10/2001 | Zylka | A61B 6/12 600/9 |
| 2001/0036246 A1 * | 11/2001 | Graumann | A61B 6/0478 378/39 |
| 2002/0051517 A1 * | 5/2002 | Schwieker | A61B 6/4429 378/196 |
| 2003/0099328 A1 * | 5/2003 | Jensen | A61B 6/08 378/198 |
| 2003/0112926 A1 * | 6/2003 | Atzinger | A61B 6/4452 378/196 |
| 2004/0066906 A1 * | 4/2004 | Hornegger | A61B 6/02 378/197 |
| 2006/0293582 A1 * | 12/2006 | Jensen | A61B 6/08 600/407 |
| 2007/0211847 A1 * | 9/2007 | Graumann | A61B 6/102 378/15 |
| 2008/0118036 A1 * | 5/2008 | Jensen | A61B 6/4441 378/198 |
| 2009/0274271 A1 * | 11/2009 | Pfister | A61B 6/12 378/62 |
| 2010/0008474 A1 * | 1/2010 | Hornung | A61B 6/4458 378/197 |
| 2012/0099697 A1 * | 4/2012 | Helm | A61B 6/02 378/4 |
| 2012/0099778 A1 * | 4/2012 | Helm | A61B 6/4476 382/132 |
| 2012/0281812 A1 * | 11/2012 | Noda | A61B 6/4233 378/62 |
| 2013/0025055 A1 * | 1/2013 | Saracen | A61B 6/548 5/601 |
| 2013/0083894 A1 * | 4/2013 | Niebler | A61B 6/4441 378/62 |
| 2013/0243160 A1 * | 9/2013 | Graumann | A61B 6/54 378/91 |
| 2013/0287171 A1 * | 10/2013 | Hibino | A61B 6/4405 378/62 |
| 2014/0033432 A1 * | 2/2014 | Marle | A61B 6/0407 5/601 |
| 2014/0105357 A1 * | 4/2014 | Shin | A61B 6/4435 378/62 |
| 2015/0085986 A1 * | 3/2015 | Dinse | A61B 6/10 378/98 |
| 2015/0131775 A1 * | 5/2015 | Yorkston | A61B 6/032 378/17 |
| 2015/0305703 A1 * | 10/2015 | Kim | A61B 6/467 378/62 |

\* cited by examiner

DEVICE FOR REMOTE FLUOROSCOPY, NEARBY FLUOROSCOPY AND RADIOLOGY

CROSS-REFERENCE TO PRIOR APPLICATIONS

This application is the U.S. National Phase application under 35 U.S.C. § 371 of International Application No. PCT/EP2016/066701, filed on Jul. 13, 2016, which claims the benefit of European Patent Application No. 15177096.3, filed on Jul. 16, 2015. These applications are hereby incorporated by reference herein.

FIELD OF THE INVENTION

The present invention relates a device for X-ray imaging, a patient table for X-ray imaging and a system for X-ray imaging.

BACKGROUND OF THE INVENTION

Generally speaking, it is of clinical benefit in X-ray imaging to be able to generate images of various intersections of a patient, however, without repositioning the patient relative to the patient support. This requires a device for X-ray imaging having a mechanical geometry capable of appropriately positioning the X-ray source and X-ray detector relative to such patient. Various geometries have been contemplated towards that extent. For example, U.S. Pat. No. 6,644,852 B2 discloses a device having two independently articulated arms supporting an X-ray tube and an X-ray detector. In addition, U.S. Pat. No. 5,155,757 discloses a C-arm having a curved sliding mechanism. However, state of the art devices rely on complex and heavy hence expensive mechanical geometries.

U.S. Pat. No. 3,281,598 A discloses an overhead support for a vertically and rotatably movable X-ray tube support arm and cooperating tiltable X-ray table.

U.S. Pat. No. 4,412,346 A discloses an X-ray photography apparatus comprising an X-ray tube and an image receiving device attached to two tilting members which are each rockably supported on the distal end portion of a traveling support frame telescopically protruding parallel to a horizontal main axis from a rotating base rotating about the main axis.

US 2014/105357 A1 discloses an X-ray apparatus including a source for emitting X-rays to an object; a detector for detecting the X-rays penetrating the object; an arm for connecting the source to the detector and moving the detector up and down according to a rotation of the source; and a controller for controlling an imaging of the object by driving the arm.

US 2003/112926 A1 discloses an X-ray apparatus that has a radiation source and a radiation receiver that are movably mounted at a stand arranged at the ceiling of an installation room.

US 2014/033432 A1 discloses a patient positioning system which employs an arm having a first portion and a second portion which is telescopic relative to the first portion.

SUMMARY OF THE INVENTION

There may be a need to provide a less complex hence less expensive mechanical geometry for X-ray imaging without compromising clinical qualities.

The object of the present invention is solved by the subject-matter of the independent claims, wherein further embodiments are incorporated in the dependent claims. It should be noted that the following described aspects of the device for X-ray imaging according to the invention apply also for the system for X-ray imaging according to the invention.

According to a first aspect of the present invention, a device for X-ray imaging is provided comprising a device mount and an arm movably connected to said device mount for rotation, relative to said device mount, around a device axis of rotation. The device for X-ray imaging furthermore comprises an X-ray source for emitting an X-ray beam and an X-ray detector. In addition, the device for X-ray imaging comprises a carrier having a U-arm geometry, wherein said U-arm geometry is provided with mutually facing portions and an intermediate portion connecting said mutually facing portions. Furthermore said mutually facing portions are configured for carrying the X-ray source and the X-ray detector, respectively. Moreover said intermediate portion is movably connected to the arm for rotation, relative to said arm, around a carrier axis of rotation substantially perpendicular to the device axis of rotation. At least one of the X-ray source and the X-ray detector is moveably connected to the carrier for mutual translation, relative to the carrier, in a direction substantially parallel to an optical axis of the device. Or the carrier is extendable in said direction substantially parallel to said optical axis such that the X-ray source and the X-ray detector are configured for mutual translation in said direction substantially parallel to said optical axis.

In this text, the term "X-ray imaging" is understood to include remote fluoroscopy, nearby fluoroscopy and radiology, all either diagnostic or interventional.

In this text, the term "U-arm geometry" is a geometry substantially having the form of a "U", that is a geometry having (i) two mutually facing portions which are substantially non-curved (for example straight) and which may but need not be mutually parallel; and (ii) a portion intermediate mutually connecting (for example via curved sections) said mutually facing portions, which intermediate portion may but need not be perpendicularly oriented relative to said mutually facing portions.

In this text, "plane" means a two-dimensional surface of infinite width and length, zero thickness and zero curvature.

In this text, "optical axis" is an imaginary line that defines the path along which the central X-ray beam during operation propagates from the X-ray source towards the X-ray detector, and along which the X-ray beam exhibits some form of symmetry.

In this text, "horizontal" means a direction and/or plane substantially perpendicular to gravity. Consequently, in this text "vertical" means a direction and/or plane substantially parallel to gravity.

In this text "substantially parallel" is understood to mean parallel including minor deviations thereof up to ±5 degrees as may be due to tolerances caused by e.g. manufacturing and the installation of the device, system and patient table according to the present invention. Likewise, in this text "substantially perpendicular" is understood to mean perpendicular including minor deviations thereof up to ±5 degrees as may be due to tolerances caused by e.g. manufacturing and the installation of the device, system and patient table according to the present invention. Similarly, in this text "equal" is understood to mean equal including minor deviations thereof up to ±5% as may be due to e.g. deviations from setpoints in control systems.

The device axis of rotation and the carrier axis of rotation enable imaging of a patient in three mutually perpendicular planes hence any plane in a three dimensional space. That is, device axis of rotation and the carrier axis of rotation enable positioning the X-ray source and X-ray detector (more precisely the optical axis of the device) in any orientation relative to the patient. This holds irrespective the position of the device mount which feasibly allows for mounting the device to a floor, a wall or a ceiling of an X-ray examination room. Herein, at least the carrier axis of rotation enables isocentric imaging. At the same time the U-arm geometry is less complex and less heavy hence less expensive compared to geometries involving a plurality of arms or a C-arm. Hence, the device for X-ray imaging according to the present invention enables imaging a patient in any plane, to a certain degree even isocentric, while omitting a complex and heavy hence expensive mechanical geometry. Namely, the device for X-ray imaging according to the present invention employs a plurality of purely rotational degrees of freedom (and optionally one or more purely translational degrees of freedom).

The device for X-ray imaging according to the present invention enables a relatively small footprint compared to state of the art fluoroscopy systems owing to its device mount. This facilitates access to the patient and hence enhances clinical workflow.

The device for X-ray imaging according to the present invention furthermore provides for a relativity unobtrusive structure owing to its arm and carrier. This enables access to the patient from all directions and also improves cleanability.

The device for X-ray imaging according to the present invention in addition enables bi-directional use because of its symmetrical geometry. This allows for installation in both left and right oriented room layouts.

In an example of the device for X-ray imaging according to the present invention, (i) the intermediate portion of the U-arm geometry is furthermore movably connected to the arm for translation, relative to said arm, along a direction substantially parallel to the device axis of rotation, or (ii) the arm is extendable in said direction substantially parallel to the device axis of rotation, and the intermediate portion of the U-arm geometry is mounted to an extremity of the arm opposite the device mount. In this text "an extremity of the arm" is understood to comprise without limitation an arm's end. Both alternatives of this example have the effect of increasing the opportunities of appropriately positioning the X-ray source and the X-ray detector relative to a patient thereby enabling the imaging of a certain clinically relevant part of the patient. Furthermore, this example enables displacing the X-ray source and the X-ray detector relative to the patient. Such displacement may for example be along a one-dimensional non-curved path which for example is beneficial for fluoroscopy as well as long-length imaging via image stitching in radiology. Such path may be vertical in case the device mount is mounted to the floor or the ceiling, or alternatively, it may be horizontal in case the device mount is installed on the wall. Given the device axis of rotation and the carrier axis of rotation, this example may also effectively realize (three-dimensional) non-curved paths of displacement.

In another example of the device for X-ray imaging according to the present invention, the arm is furthermore movably connected to the device mount for translation, relative to said device mount, along a direction substantially perpendicular to the device axis of rotation. This example has the effect of further increasing the opportunities of appropriately positioning the X-ray source and the X-ray detector relative to a patient. Furthermore, this device enables displacing the X-ray source and the X-ray detector relative to the patient along a path during X-ray imaging for the purpose of fluoroscopy as well as image stitching. Such path may be horizontal in case the device mount is mounted to the floor or the ceiling, or alternatively, it may be vertical in case the device mount is installed on the wall. If this example of the device for X-ray imaging is used in conjunction with the aforementioned example, a device for X-ray imaging will be obtained capable of displacing the X-ray source and the X-ray detector relative to the patient along an inclined (i.e. neither horizontal nor vertical) non-curved path thereby further increasing imaging options. In particular, this device allows for useful application in fluoroscopy in which for some clinical purposes the propagation of a radiocontrast agent under the influence of gravitation in a patient is examined. Given the device axis of rotation and the carrier axis of rotation, this example may also effectively realize (three-dimensional) non-curved paths of displacement.

Another example of the device for X-ray imaging according to the present invention furthermore comprises a guiding, wherein the device mount is movably connected to said guiding for translation, relative to said guiding, along a direction substantially perpendicular to the device axis of rotation. This example has the effect of further increasing the opportunities of appropriately positioning the X-ray source and the X-ray detector relative to a patient. Herein, the guiding typically allows for displacement over significant distance, which may for example be used to position the device in its entirety.

In another example of the device for X-ray imaging according to the present invention, the device mount is a ceiling mount such that the device axis of rotation is substantially parallel to gravitation. This example has the effect of a ceiling suspension hence the prevention of floor contact which increases cleanability and reachability. Alternatively, the device mount may be a wall mount such that the device axis of rotation is substantially perpendicular to gravitation, or the device mount may be a floor mount such that the device axis of rotation is substantially parallel to gravitation. In an alternative example of the device for X-ray imaging according to the present invention, the device furthermore comprises a console for connecting the arm to the device mount such that the device is a wall mount whereas the device axis of rotation is substantially parallel to gravitation.

In the device for X-ray imaging according to the present invention, (i) at least one of the X-ray source and the X-ray detector is moveably connected to the carrier for mutual translation, relative to the carrier, in a direction substantially parallel to an optical axis of the device, or (ii) the carrier is extendable in said direction substantially parallel to an optical axis of the device such that the X-ray source and the X-ray detector are configured for mutual translation in the direction substantially parallel to said optical axis. Both alternatives of this example provide for a controllable source-to-image-distance ("SID") which is instrumental for various clinical examinations.

In another example of the device for X-ray imaging according to the present invention, (i) the X-ray source and the X-ray detector are moveably connected to the carrier for translation, relative to the carrier, along a direction substantially parallel to an optical axis of the device, or (ii) the carrier is extendable in said direction substantially parallel to the optical axis such the X-ray source and the X-ray detector are configured for translation in said direction substantially parallel to said optical axis. In this example the device for X-ray imaging furthermore comprises a translation controller configured for synchronizing (a) said translation of the X-ray source and (b) said translation of the X-ray detector, such that a distance between said X-ray source and said X-ray detector is constant during operation. This example provides for a controllable source-to-iso-center-distance ("SIsoD") while keeping SID constant, which is instrumental for various clinical examinations. A notable advantage of this example is in increasing patient safety by positioning the X-ray source at a greater distance from the patient while leaving SID unchanged.

In another example of the device for X-ray imaging according to the present invention, the X-ray detector is movably connected to the carrier for rotation, relative to the carrier, around a detector axis substantially parallel to the carrier axis of rotation, furthermore comprising a rotation controller configured for synchronizing (i) the rotation of the X-ray detector around the detector axis of rotation and the (ii) rotation of the carrier around the carrier axis of rotation, for maintaining an orientation of an X-ray sensitive area of the X-ray detector constant during operation. This example has the effect of enabling oblique X-ray imaging. Furthermore this example enables maintaining a constant orientation of the X-ray sensitive area of the X-ray detector while changing the orientation of the optical axis (by rotation of the carrier around the carrier axis of rotation) relative to said X-ray sensitive surface. Accordingly this example furthermore has the effect of making the device suitable for X-ray tomography in general and tomosynthesis more in particular.

In another example of the device for X-ray imaging according to the present invention, the X-ray source is movably connected to the carrier for rotation, relative to the carrier, around a source axis of rotation substantially parallel to the carrier axis of rotation. This example enables a free exposure in which an additional X-ray detector, freely positionable by the radiologist, is being employed.

In another example of the device for X-ray imaging according to the present invention, (i) at least one of the X-ray source and the X-ray detector is moveably connected to the carrier for translation relative to the carrier in a direction substantially perpendicular to the optical axis of the device, or (ii) at least one of the mutually facing portions of the U-arm geometry are extendable in a direction substantially perpendicular to the optical axis of the device such that the X-ray source and the X-ray detector are configured for mutual translation in said direction substantially perpendicular to said optical axis. This example has the effect of realizing a mutual displacement of the X-ray source and the X-ray detector in a plane substantially perpendicular to the optical axis, thereby enabling the exposure of a predefined subset of the X-ray detector's X-ray sensitive surface.

In another example of the device for X-ray imaging according to the present invention, the X-ray detector is a dynamic X-ray detector. This example has the effect of making the device for X-ray imaging suitable for fluoroscopy in addition to radiology. More specifically, this example enables performing nearby fluoroscopy, remote fluoroscopy as well as radiology. In nearby fluoroscopy the X-ray source is arranged underneath a horizontally or slightly inclined positioned patient whereas the X-ray detector is arranged above such patient. Nearby fluoroscopy allows for appropriately reducing the exposure of the radiologist to scattered X-ray and hence allows the radiographer to be present nearby the patient. In remote fluoroscopy the X-ray source is arranged above such patient whereas the X-ray detector is arranged underneath such patient. Remote fluoroscopy necessitates the radiographer to be remote from the patient in order to prevent from exposure to excessive X-ray scatter. Radiology typically employs a configuration similar to remote fluoroscopy. By rotating the carrier around the carrier axis of rotation, the device can switch between nearby and remote fluoroscopy (and hence radiology). Accordingly the device for X-ray imaging circumvents the need for employing separate devices for nearby fluoroscopy and remote fluoroscopy, respectively. This not only saves costs in terms of purchase price and valuable examination room space, but also facilitates clinical work flow. This example thus has the advantage of integrating three imaging modalities into a single device.

In another example of the device for X-ray imaging according to the present invention, the carrier is movably connected to the arm for translation relative to the arm in a direction substantially perpendicular to the device axis of rotation as well as the carrier axis of rotation.

According to a second aspect of the present invention, a system for X-ray imaging is provided. The system comprises the device for X-ray imaging according to the present invention and a patient table for X-ray imaging. The patient table comprises a floor mount and a leg movably connected to said floor mount for rotation, relative to said floor mount, around a leg axis of rotation being horizontal. The patient table furthermore comprises a patient support movably connected to said leg for rotation, relative to the leg, around a support axis of rotation being substantially parallel to the leg axis of rotation. Because the leg axis of rotation and the support axis of rotation are in mutually substantially parallel planes, by providing mutually opposite rotations along said axes such that eventually the leg is in an almost horizontal position, the patient table is capable of positioning the patient support extremely close to the floor. This quality is highly beneficial for disabled patients. It is furthermore capable of addressing regulatory requirements as imposed by disability acts.

An example of the patient table in a system according to the present invention comprises a rotation controller for synchronizing the rotation around the leg axis of rotation and the rotation of the patient support around the support axis of rotation relative to the leg for maintaining the patient support in a horizontal orientation during rotation of the leg.

In another example of the patient table n a system according to the present invention, the patient support is connected to the leg at a headboard or a foodboard. In this example the leg does not interfere with the scannable area. Consequently, this example has the effect of realizing a very large scannable area, namely, a scannable area that encompasses the patient in full.

In another example of the patient table n a system according to the present invention, the patient support is provided with a foot support mounted at the foodboard of the patient support. This example enables safely positioning a patient in a non-horizontal orientation e.g. a titled or even a vertical orientation.

In another example of the patient table n a system according to the present invention, the leg is extendable along a direction substantially perpendicular to the leg axis of rotation.

In another example of the patient table n a system according to the present invention, the patient support is movably connected to the leg, for rotation relative to said leg, around a tilting axis of rotation being substantially perpendicular to the support axis of rotation and parallel to the patient support. This example has the effect of being able to switch from posterior-anterior imaging to anterior-posterior imaging, and vice versa, without requiring the patient (lying on the patient support) to move.

In another example of the patient table n a system according to the present invention, the patient table furthermore comprises a rotation controller for synchronizing (i) the rotation around the leg axis of rotation and (ii) the rotation of the patient support around the support axis of rotation, for maintaining the patient support in a predetermined (e.g. horizontal) orientation during rotation of the leg around the leg axis of rotation. This example enables changing height of the patient table without affecting its orientation.

In an example of the system for X-ray imaging according to the present invention, the system comprises a system controller for synchronizing (i) the rotation of the patient support around the support axis of rotation and (ii) the rotation of the carrier around the carrier axis of rotation for maintaining the orientations of said patient support and said carrier mutually substantially perpendicular during orientation. This example is particularly useful for fluoroscopy (either remote or nearby) procedures. That is, during a fluoroscopy procedure a patient often is required to be positioned in a non-horizontal i.e. titled position such that the propagation of a tracer fluid in the patient under the influence of gravity can be monitored. By mutually synchronizing the rotations of the patient support and the carrier, such monitoring is effectively enabled for a broad range of patient tilt angles for remote as well as nearby fluoroscopy. Accordingly, this example is arranged for maintaining the orientations of the patient support and the X-ray sensitive area of the X-ray detector mutually substantially parallel during operation.

BRIEF DESCRIPTION OF THE DRAWINGS

Particular aspects of the present invention will now be explained with reference to the examples described hereinafter in connection with the accompanying drawings in which identical parts are designated in the same manner.

DETAILED DESCRIPTION OF THE EMBODIMENTS

Figure 1:
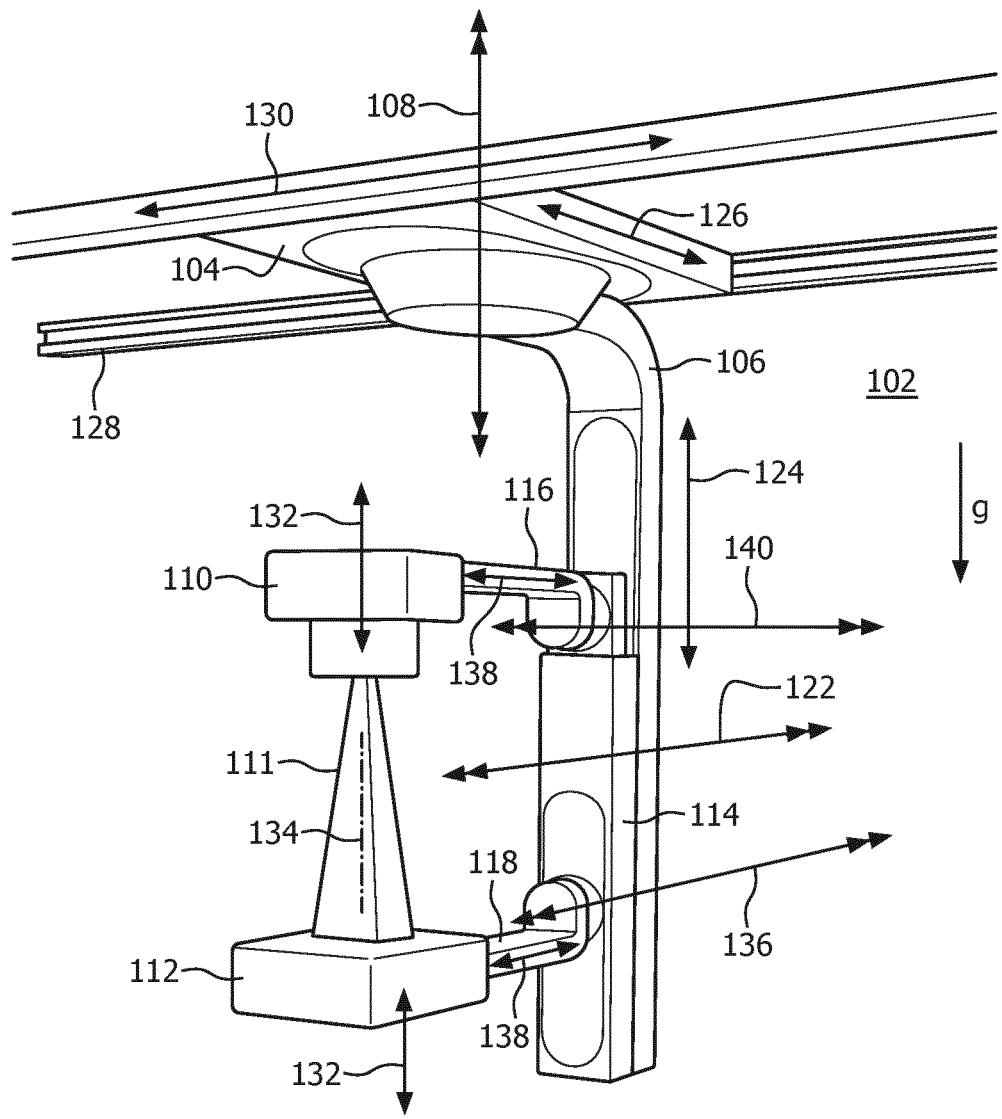
FIG. 1 schematically depicts a device for X-ray imaging according to the present invention.

FIG. 1 schematically depicts a device 102 for X-ray imaging. The device 102 comprises a device mount 104 and an arm 106 movably connected to said device mount 104 for rotation, relative to said device mount 104, around a device axis of rotation 108. In a specific example, the amount of rotation around the device axis of rotation 108 realizable by the arm 106 amounts up to ±360 degrees. In a specific example, such rotational degree of freedom around the device axis of rotation 108 is realized by an actuator known per se to the person skilled in the art. In such specific example, an axis extending from the arm 106 is supported by a bearing (known per se to the person skilled in the art) accommodated in the device mount 104, and wherein the actuator (accommodated in the device mount 104 as well) drives (either directly or via a transmission) the axis extending from the arm 106. The device 102 furthermore comprises an X-ray source 110 for emitting an X-ray beam 111 and an X-ray detector 112. In a specific example of the device 102, said X-ray detector 112 is a dynamic X-ray detector such that the device 102 is configured for performing nearby as well as remote fluoroscopy in addition to radiology. In addition the device comprises a carrier 114 having a U-arm geometry, wherein said U-arm geometry is provided with mutually facing portions 116 and 118, and an intermediate portion 120 connecting said mutually facing portions 116 and 118. Herein the mutually facing portions 116 and 118 are configured for carrying the X-ray source 110 and the X-ray detector 112, respectively. The intermediate portion 120 is movably connected to the arm 106 for rotation, relative to said arm 106, around a carrier axis of rotation 122 substantially perpendicular to the device axis of rotation 108. In a specific example, the amount of rotation around the carrier axis of rotation 122 realizable by the carrier 114 amounts up to ±310 degrees. In this specific example, the device mount 104 is a ceiling mount such that the device axis of rotation 108 is substantially parallel to gravitation g.

Figure 2:
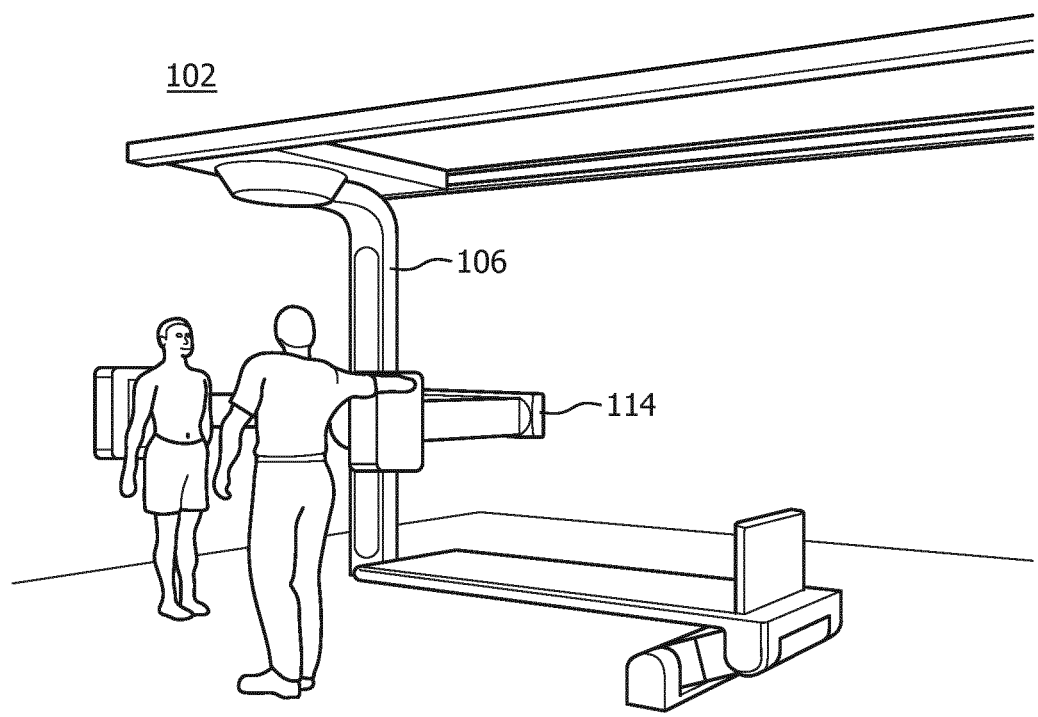
FIG. 2 schematically depicts a configuration of the device for X-ray imaging wherein the carrier, during operation, has been rotated.

FIG. 2 schematically depicts a configuration of device 102 in which the carrier 114, compared to the configuration as depicted in FIG. 1, during operation is rotated 90 degrees along the carrier axis of rotation 122 for the purpose of imaging a patient 101 in standing position.

Figure 3:
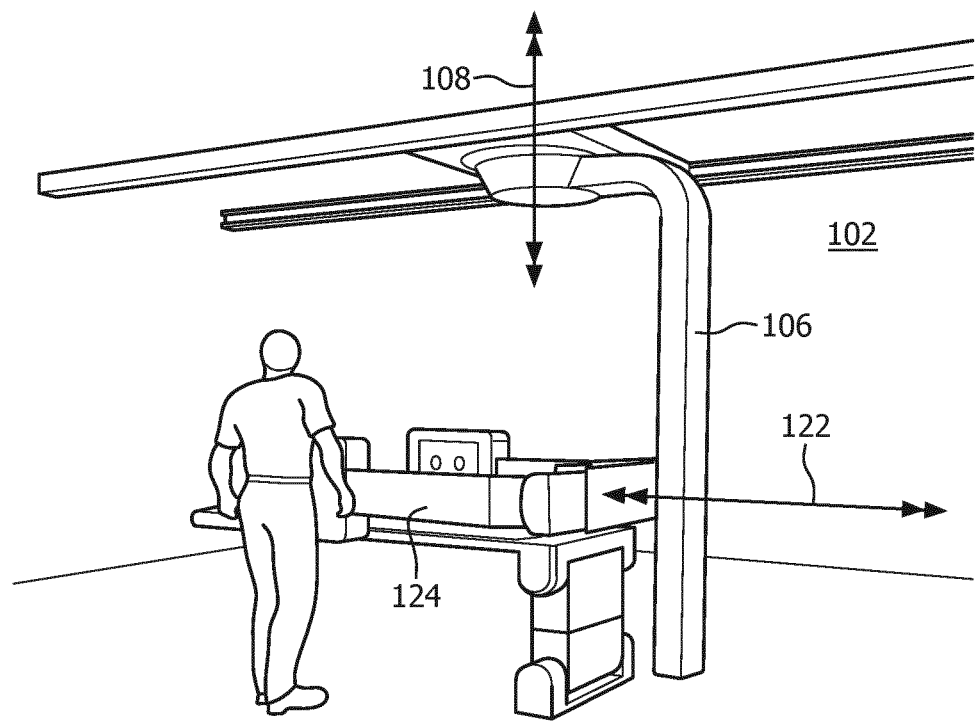
FIG. 3 schematically depicts a configuration of the device for X-ray imaging wherein the carrier and the arm, during operation, have been rotated.

FIG. 3 schematically depicts another configuration of device 102 in which the arm 106, compared to the configuration as depicted in FIG. 2, during operation is rotated 90 degrees along the device axis of rotation 108 for the purpose of imaging a patient (not shown) in horizontal position from a lateral viewpoint.

Referring to FIG. 1 again, in another specific example of the device 102, the intermediate portion 120 of the U-arm geometry is furthermore movably connected to the arm 106 for translation, relative to said arm 106, along a direction 124 substantially parallel to the device axis of rotation 108. In a specific example, the amount of displacement along the direction 124 realizable by the carrier 114 amounts to 1933 mm in total.

Figure 4:
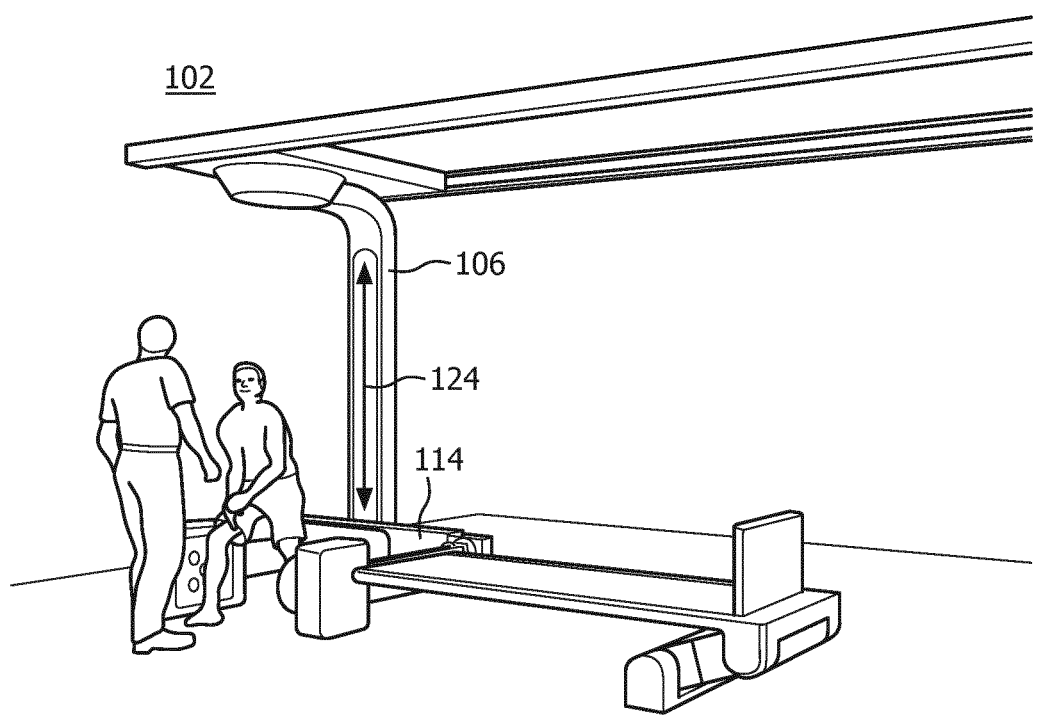
FIG. 4 schematically depicts a configuration of the device for X-ray imaging wherein the carrier, during operation, has been rotated and translated downwardly.

FIG. 4 schematically depicts a configuration of device 102 in which the carrier 114, compared to the configuration as depicted in FIG. 2, during operation is translated downwardly (basically to such extent that the X-ray detector 112 contacts the floor) along the direction 124 in order to image a patient's ankle, lower leg and/or knee.

Referring to FIG. 1 again, in another specific example of the device 102, the arm 106 is furthermore movably connected to the device mount 104 for translation, relative to said device mount 104, along a direction 126 substantially perpendicular to the device axis of rotation 108. In a specific example, the amount of displacement along the direction 126 realizable by the arm 106 amounts to 520 mm in total.

Another specific example of the device 102 comprises a guiding 128, wherein the device mount 104 is movably connected to said guiding 128 for translation, relative to said guiding 128, along a direction 130 substantially perpendicular to the device axis of rotation 108. In a specific example, the amount of displacement along the direction 130 realizable by the device mount 104 amounts to 4150 mm in total.

In another specific example of the device 102, the carrier 114 is extendable in a direction 132 substantially parallel to an optical axis 134 of the device 102 such that the X-ray source 110 and the X-ray detector 112 are configured for mutually translating along the direction 132. In a specific example, the amount of displacement along the direction 132 realizable by the X-ray source 110 and the X-ray detector 112 amounts to 393 mm and 706 mm, respectively, thereby offering the option to alter SID up to 1099 mm in total.

In another specific example of the device 102, the carrier is extendable in the direction substantially parallel to the optical axis of the device such that both the X-ray source 110 and the X-ray detector 112 are configured for simultaneously moving along the direction 132. In this example the device 102 furthermore comprises a translation controller (not shown) configured for synchronizing (a) said translation of the X-ray source 110 and (b) said translation of the X-ray detector 112, such that a distance between said X-ray source 110 and said X-ray detector 112 is constant during operation. The controller may be a controller known per se to the person skilled in the art such as a proportional-integrating-derivative ("PID") controller possibly in combination with feed forward.

In another specific example of the device 102, the X-ray detector 112 is movably connected to the carrier 106 for rotation, relative to the carrier 106, around a detector axis of rotation 136 substantially parallel to the carrier axis of rotation 122. In this specific example, the device 102 furthermore comprises a rotation controller (not shown) configured for synchronizing (i) the rotation of the X-ray detector 112 around the detector axis of rotation 134 and the (ii) rotation of the carrier 106 around the carrier axis of rotation 122, such that said rotations have equal magnitude and opposite direction during operation. In a specific example, the amount of rotation around the detector axis of rotation 122 realizable by the X-ray detector 112 amounts up to ±50 degrees.

Figure 5:
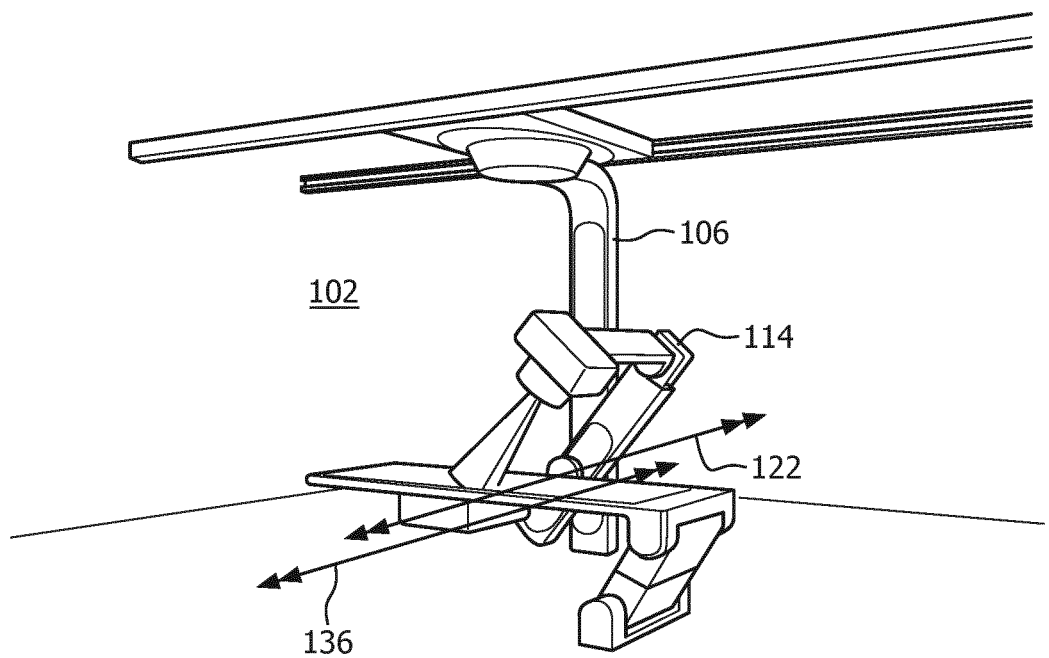
FIG. 5 schematically depicts a configuration of the device for X-ray imaging wherein the carrier, during rotation, has been rotated relative to the arm, and wherein the X-ray detector, during operation, has been rotated relative to the carrier thereby maintaining a horizontal position.

FIG. 5 schematically depicts a configuration of device 102 in which the carrier 114, compared to the configuration as depicted in FIG. 1, during operation is rotated along the carrier axis of rotation 122 whereas the X-ray detector 112 during operation is rotated an equal amount in an opposite direction along the detector axis of rotation 136 relative to the carrier 114. Consequently the X-ray sensitive surface of the X-ray detector 112 maintains its horizontal orientation during operation. This type of configuration is suitable for performing oblique X-ray, X-ray tomography and tomosynthesis.

Returning to FIG. 1, in another specific example of the device 102, at least one of the mutually facing portions 116 and 118 is extendable in a direction 138 substantially perpendicular to the optical axis 134 of the device 102 such that the X-ray source 110 and the X-ray detector 112 are configured for mutual translation in said direction 138. In this specific example, direction 138 is substantially parallel to the carrier axis of rotation 122. In an alternative example, direction 138 is generally in a plane perpendicular to the optical axis, including the scenario in which direction 138 is substantially perpendicular to the carrier axis of rotation.

In another specific example of the device 102, the X-ray source 110 is movably connected to the carrier 114 for rotation, relative to the carrier 114, around a source axis of rotation 140 substantially parallel to the carrier axis of rotation 122.

Figure 6:
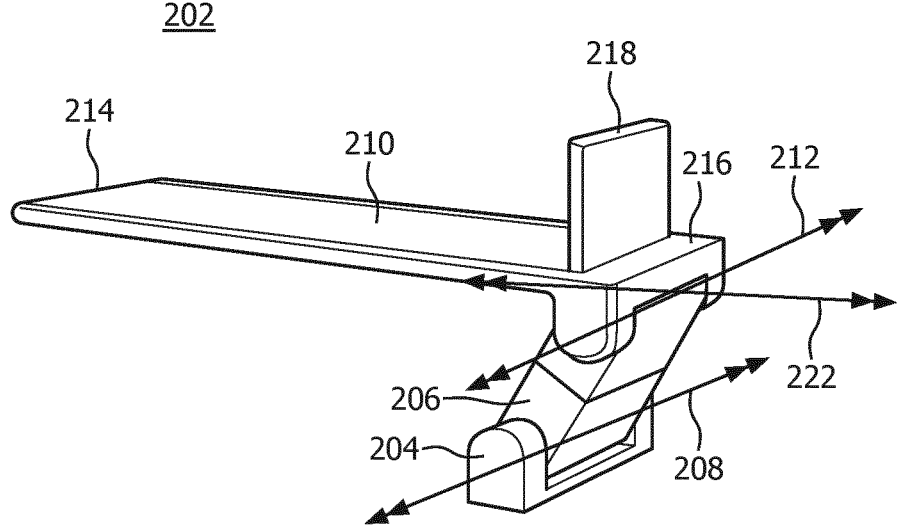
FIG. 6 schematically depicts a patient table for X-ray imaging according to the present invention.

FIG. 6 schematically depicts a patient table 202 for use with the device 102. The patient table 202 comprises a floor mount 204 and a leg 206 movably connected to said floor mount for rotation, relative to said floor mount, around a leg axis of rotation 208 being horizontal. The patient table 202 furthermore comprises a patient support 210 movably connected to said leg 206 for rotation, relative to the leg 206, around a support axis of rotation 212 being in a plane substantially parallel to the leg axis of rotation 208. The patient support may be manufactured from an X-ray transparent material known to the person skilled in the art such as high pressure laminate.

In a specific example, the patient table furthermore comprises a rotation controller (not shown) for synchronizing (i) the rotation around the leg axis of rotation 208 and (ii) the rotation of the patient support 210 around the support axis of rotation 212, for maintaining the patient support 210 in a predetermined (e.g. horizontal) orientation during rotation of the leg 206 around the leg axis of rotation 208.

Figure 7:
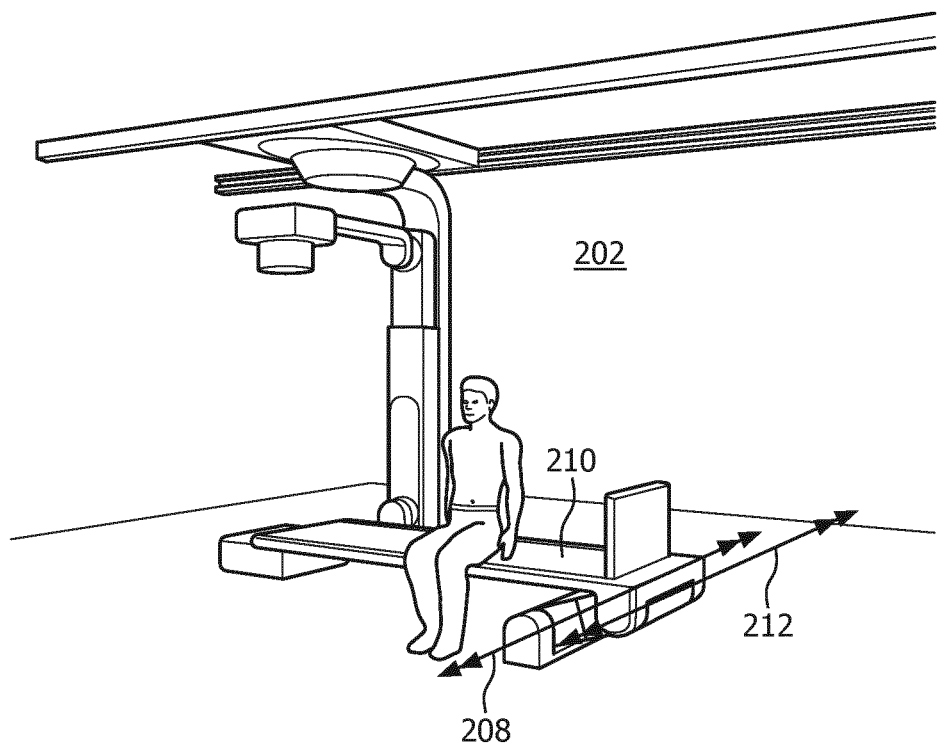
FIG. 7 schematically depicts a configuration of the patient table for X-ray imaging wherein the leg and the patient support, during operation, have been rotated.

FIG. 7 schematically depicts a configuration of the patient table 202 wherein, during operation, the leg 206 has been rotated around the leg axis of rotation 208 and the patient support 210 has been rotated around the support axis of rotation 212 relative to the leg 206, in a synchronized manner, such that the patient support 210 remains horizontal while it is being moved downwardly.

Referring to FIG. 6, in another specific example of the patient table 202 the patient support 210 is connected to the leg 206 at its headboard 214 or its foodboard 216.

In another specific example of the patient table 202, the patient support 210 is provided with a foot support 218 mounted at the foodboard 216 of the patient support.

Figure 8:
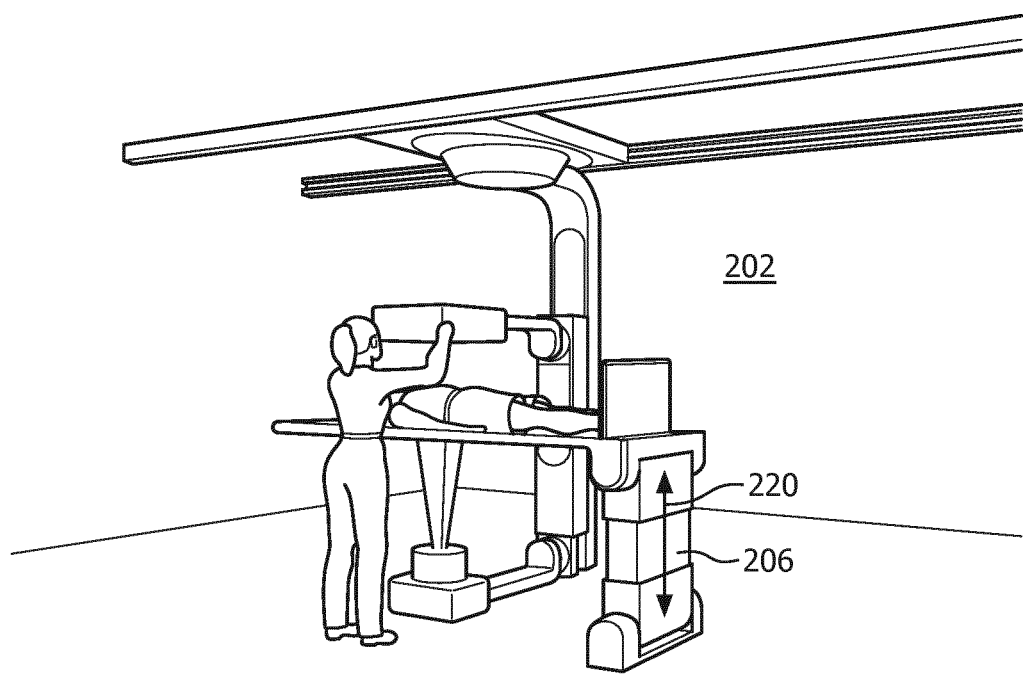
FIG. 8 schematically depicts a configuration of the patient table for X-ray imaging wherein the leg, during operation, has been extended.

In another specific example of the patient table 202, the leg 206 is extendable. FIG. 8 schematically depicts a configuration of the patient table 202 wherein, during operation, the leg 206 has been extended along the direction 220 substantially perpendicular to the leg axis of rotation 206 in order to elevate the patient support 210 up to a height feasible e.g. for a radiologist to perform his tasks.

Referring to FIG. 6, in another specific example of the patient table 202, the patient support 210 is movably connected to the leg 206, for rotation relative to said leg 206, around a tilting axis of rotation 222 being substantially perpendicular to the support axis of rotation 212 and being parallel to the patient support 210.

Figure 9:
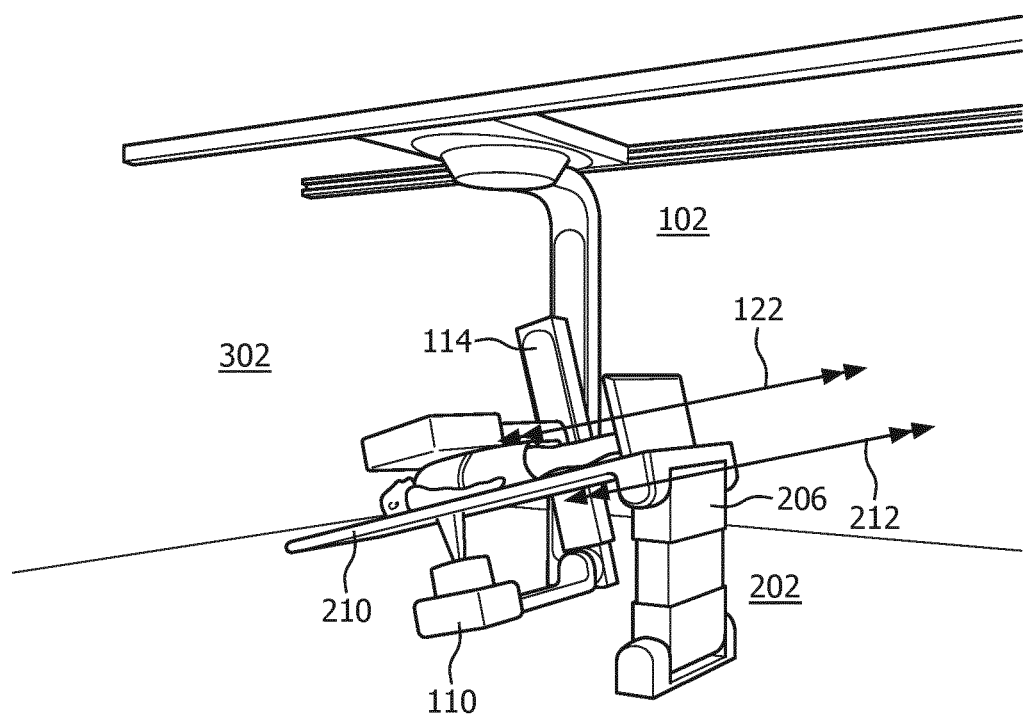
FIG. 9 schematically depicts a system for X-ray imaging according to the present invention.

FIG. 9 schematically depicts a system 302 for X-ray imaging comprising the device 102 for X-ray imaging and the patient table 202 for X-ray imaging.

In an example of the system 302, the system 302 furthermore comprises a system controller (not shown) for synchronizing (i) the rotation of the patient support 210 around the support axis of rotation 212 and (ii) the rotation of the carrier 114 around the carrier axis of rotation 122, for maintaining the orientations of said patient support 210 and said carrier 114 mutually substantially perpendicular during orientation. More specifically, FIG. 9 schematically depicts a configuration of the system 302 as used for the purpose of nearby fluoroscopy in which the X-ray detector 110 is installed underneath the patient. In this configuration, the patient support 210 is tilted i.e. rotated around the support axis of rotation 212 whereas the carrier 114 is accordingly rotated around the carrier axis of rotation 122. This configuration of the system allows for investigation the propagation of a tracer fluid in a patient by making use of gravity.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for X-ray imaging, comprising:
a device mount;
an arm movably connected to the device mount for rotation, relative to the device mount, around a device axis of rotation;
an X-ray source for emitting an X-ray beam;
an X-ray detector;
a rotation controller; and
a carrier having a U-arm geometry, wherein the U-arm geometry is provided with mutually facing portions and an intermediate portion connecting the mutually facing portions, wherein the mutually facing portions are configured for carrying the X-ray source and the X-ray detector, respectively, and wherein the intermediate portion is movably connected to the arm for rotation, relative to the arm, around a carrier axis of rotation substantially perpendicular to the device axis of rotation;
wherein at least one of the X-ray source and the X-ray detector is moveably connected to the carrier for mutual translation, relative to the carrier, in a direction substantially parallel to an optical axis of the device; and
wherein the X-ray detector is movably connected to the carrier for rotation, relative to the carrier, around a detector axis of rotation substantially parallel to the carrier axis of rotation, wherein the rotation controller is configured to synchronize a first rotation of the X-ray detector around the detector axis of rotation and a second rotation of the carrier around the carrier axis of rotation, such that the first and second rotations have an equal magnitude and are in opposite directions during operation.

2. The device according to claim 1, wherein
the intermediate portion of the U-arm geometry is furthermore movably connected to the arm for translation, relative to the arm, along a direction substantially parallel to the device axis of rotation, or
the arm is extendable in a direction substantially parallel to the device axis of rotation and wherein the intermediate portion of the U-arm geometry is mounted to an extremity of the arm opposite the device mount.

3. The device according to claim 1, wherein the arm is furthermore movably connected to the device mount for translation, relative to the device mount, along a direction substantially perpendicular to the device axis of rotation.

4. The device according to claim 1, further comprising a guiding, wherein the device mount is movably connected to the guiding for translation, relative to the guiding, along a direction substantially perpendicular to the device axis of rotation.

5. The device according to claim 1, wherein the device mount is a ceiling mount such that the device axis of rotation is substantially parallel to gravitation.

6. The device according to claim 1, wherein
the X-ray source and the X-ray detector are moveably connected to the carrier for translation, relative to the carrier, along a direction substantially parallel to the optical axis of the device, or
wherein the carrier is extendable in the direction substantially parallel to the optical axis such the X-ray source and the X-ray detector are configured for translation in the direction substantially parallel to the optical axis, further comprising a translation controller configured for synchronizing:
the translation of the X-ray source; and
the translation of the X-ray detector,
such that a distance between the X-ray source and the X-ray detector is constant during operation.

7. The device according to claim 6, wherein
at least one of the X-ray source and the X-ray detector is moveably connected to the carrier for translation relative to the carrier in a direction substantially perpendicular to the optical axis of the system, or
wherein at least one of the mutually facing portions are extendable in the direction substantially perpendicular to the optical axis such that the X-ray source and the X-ray detector are configured for mutual translation in the direction substantially perpendicular to the optical axis.

8. The device according to claim 1, wherein the X-ray detector is a dynamic X-ray detector.

9. A system for X-ray imaging, comprising:
a device for X-ray imaging, comprising:
a device mount;
an arm movably connected to the device mount for rotation, relative to the device mount, around a device axis of rotation;
an X-ray source for emitting an X-ray beam;
an X-ray detector;
a rotation controller; and
a carrier having a U-arm geometry, wherein the U-arm geometry is provided with mutually facing portions and an intermediate portion connecting the mutually facing portions, wherein the mutually facing portions are configured for carrying the X-ray source and the X-ray detector, respectively, and wherein the intermediate portion is movably connected to the arm for rotation, relative to the arm, around a carrier axis of rotation substantially perpendicular to the device axis of rotation;
wherein at least one of the X-ray source and the X-ray detector is moveably connected to the carrier for mutual translation, relative to the carrier, in a direction substantially parallel to an optical axis of the device; and wherein the X-ray detector is movably connected to the carrier for rotation, relative to the carrier, around a detector axis of rotation substantially parallel to the carrier axis of rotation, wherein the rotation controller is configured to synchronize a first rotation of the X-ray detector around the detector axis of rotation and a second rotation of the carrier around the carrier axis of rotation, such that the first and second rotations have an equal magnitude and are in opposite directions during operation, and;

a patient table for X-ray imaging, comprising:

a floor mount;

a leg movably connected to the floor mount for rotation, relative to the floor mount, around a leg axis of rotation being horizontal; and a patient support movably connected to the leg for rotation, relative to the leg, around a support axis of rotation being substantially parallel to the leg axis of rotation.

10. The system according to claim 9, wherein the patient support is connected to the leg at a headboard or a footboard.

11. The system according to claim 9, wherein the patient support is provided with a foot support mounted at a footboard of the patient support.

12. The system according to claim 9, wherein the leg is extendable along a direction substantially perpendicular to the leg axis of rotation.

* * * * *